(12) United States Patent
Dolatkhani et al.

(10) Patent No.: US 11,535,695 B2
(45) Date of Patent: Dec. 27, 2022

(54) POLYURETHANE GELLING AGENT

(71) Applicant: POLYMEREXPERT SA, Pessac (FR)

(72) Inventors: Marc Dolatkhani, Cestas (FR); Marie Odile Hecht, Merignac (FR); Eric Lutz, Pessac (FR); Anne Pagnoux, Le Barp (FR)

(73) Assignee: POLYMEREXPERT SA, Pessac (FR)

( * ) Notice: Subject to any disclaimer, the term of this patent is extended or adjusted under 35 U.S.C. 154(b) by 369 days.

(21) Appl. No.: 16/500,859

(22) PCT Filed: Apr. 4, 2018

(86) PCT No.: PCT/FR2018/050841
§ 371 (c)(1),
(2) Date: Oct. 4, 2019

(87) PCT Pub. No.: WO2018/185432
PCT Pub. Date: Oct. 11, 2018

(65) Prior Publication Data
US 2020/0109231 A1    Apr. 9, 2020

(30) Foreign Application Priority Data
Apr. 4, 2017  (FR) ..................... 1752933

(51) Int. Cl.
| | |
|---|---|
| C08G 18/36 | (2006.01) |
| A61K 8/04 | (2006.01) |
| A61K 8/87 | (2006.01) |
| A61K 9/06 | (2006.01) |
| C08G 18/32 | (2006.01) |
| C08G 18/68 | (2006.01) |
| C08G 18/73 | (2006.01) |

(52) U.S. Cl.
CPC .............. *C08G 18/36* (2013.01); *A61K 8/042* (2013.01); *A61K 8/87* (2013.01); *A61K 9/06* (2013.01); *C08G 18/3206* (2013.01); *C08G 18/68* (2013.01); *C08G 18/73* (2013.01); *C08G 2220/00* (2013.01)

(58) Field of Classification Search
CPC ..... C08G 18/36; C08G 18/68; C08G 18/3206
See application file for complete search history.

(56) References Cited

U.S. PATENT DOCUMENTS

2013/0005936 A1\*  1/2013  Cramail .................... C11C 3/04
528/75

FOREIGN PATENT DOCUMENTS

| WO | 2011030075 A1 | 3/2011 |
| WO | 2014044809 A1 | 3/2014 |
| WO | 2014072629 A1 | 5/2014 |
| WO | 2016090081 A1 | 6/2016 |

OTHER PUBLICATIONS

International Search Report dated Jun. 21, 2018 for PCT/FR2018/050841 and English translation.

\* cited by examiner

*Primary Examiner* — Michael L Leonard
(74) *Attorney, Agent, or Firm* — Lucas & Mercanti, LLP

(57) ABSTRACT

The invention relates to new oil gelling polyurethanes useful for preparing clear gels in organic media (oils, solvents) and to a process for their preparation. The invention also relates to the gels formed from these gelling polyurethanes and to compositions containing them, in particular cosmetic compositions.

17 Claims, No Drawings

POLYURETHANE GELLING AGENT

CROSS REFERENCE TO RELATED APPLICATION

This Application is a 371 of PCT/FR2018/050841 filed on Apr. 4, 2018 which, in turn, claimed the priority of French Patent Application No. 1752933 filed on Apr. 4, 2017, both applications are incorporated herein by reference.

The invention relates to the preparation of new transparent gels in organic media (oils, solvents) from new polyurethane derivatives, as well as a process for their preparation. The invention also relates to the gels formed from these gelling polyurethanes, as well as compositions containing same, in particular cosmetic compositions.

The process according to the invention makes it possible, by implementing the formation of an isocyanate derivative having a high molar mass from an estolide (compound of the fatty acid polyester type derived from hydroxylated oils), chain extension and chain-end functionalization, to obtain a gelling polyurethane compound suitable for forming gels having the properties sought.

A subject of the invention is also the gels obtained from these gelling polyurethanes. These gels are characterized by their transparency, their low gelling polyurethane content, their dispersion ability at temperatures less than 85° C. and their thermoreversible and shear-thinning nature.

In the case of the gelling of cosmetic oils, the gelling polyurethane must meet different specific criteria. For reasons of cost, during its use in a cosmetic product, the gelling polyurethane must firstly be capable of gelling the organic phase at a low concentration, i.e. less than 5% by weight. In addition, an important aspect for a cosmetic application is the feel of the product. In fact, incorporation of the gelling agent must not result in a grainy effect that is too pronounced in the cosmetic product.

Gelling compounds having these properties are thus sought.

The esterification of castor oil derivatives is described, in particular, in application WO2014/044809, for the synthesis of prepolymers which can be used for the preparation of polymers used as additives in a poly(lactic acid) matrix. The polyurethanes obtained from these estolides comprise polyester chain-end groups, and/or do not comprise a chain extension unit, in particular of the 1,10-decanediol type. For this reason, they do not have the gelling properties sought.

Application WO2011/030075 describes the preparation of polyurethanes having a low molar mass from castor oil estolides. These compounds are used for the preparation of rigid or flexible foams and do not comprise a chain extension unit, and thus do not have the capacity to gel oils or solvents.

Application WO2016/090081 describes the preparation of polyurethanes which can be used for the gelling of oils. These polyurethanes are prepared mainly from petrosourced polymers (i.e. prepared from products originating from the petroleum industry), such as polybutadiene. The synthesis of polyurethanes from polyesters is envisaged, but only from the reaction of a glycol with a carboxylic acid ester, and without specifying the biosourced (i.e. natural origin) or non-biosourced nature of the monomers. In addition, this application describes single-step reactions involving the possible formation of byproducts that are insoluble in the oils, which can affect the viscosity and the transparency of the gels obtained from these gelling polyurethanes in the presence of oils.

It has now been found that new polyurethane derivatives, prepared from estolides of natural origin and comprising a chain extension unit, were particularly suitable for the gelling of organic oils, and made it possible to obtain a gel having the qualities sought, in particular, for a cosmetic application.

By "natural origin" is meant a product that is entirely or partially prepared from materials of natural origin.

The content of natural origin of the polyurethane, expressed as a percentage by weight, can be calculated, in particular, according to the standard NF ISO 16128-2.

Advantageously, these new polyurethane derivatives can be prepared by a synthesis process comprising a step of functionalization of an estolide-diol by a diisocyanate derivative, followed by a step of adding the chain extension unit.

The invention thus relates to polyurethane compounds of formula (I)

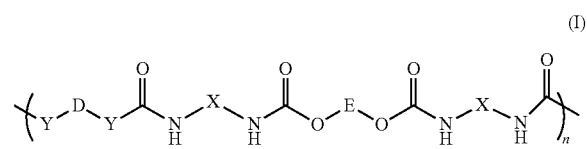

in which

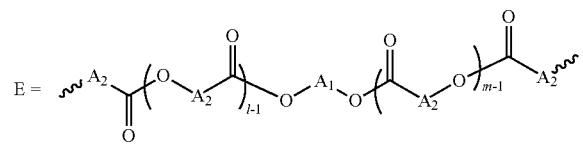

$A_1$ represents a linear or branched alkyl radical, comprising from 2 to 20 carbon atoms, preferably from 2 to 12, and in particular from 2 to 6, said radical optionally comprising one or more unsaturations, optionally being interrupted by at least one heteroatom selected from O, N and S, and being optionally substituted by at least one substituent —OAlk, Alk representing an alkyl group comprising from 1 to 10 carbon atoms;

$A_2$ represents a linear or branched alkyl radical, comprising from 2 to 20 carbon atoms, preferably from 5 to 18, and preferentially from 6 to 17 carbon atoms, said radical optionally comprising one or more unsaturations, and optionally being substituted by at least one substituent —OAlk, Alk representing an alkyl group comprising from 1 to 10 carbon atoms;

l and m represent, independently of one another, an integer from 1 to 20, preferably from 1 to 10, the sum of l+m being, preferably, from 2 to 20;

n is an integer from 1 to 20, preferably from 2 to 8;

D represents a linear or branched alkyl radical, comprising from 2 to 40 carbon atoms, preferably 6 to 14 carbon atoms, said radical optionally comprising one or more unsaturations;

X is a linear or branched alkyl radical, having or not having unsaturations, comprising from 2 to 20 carbon atoms;

Y represents an atom or a group selected from: O, NH, S and C(O)O.

Among the compounds of formula (I), those in which at least one of the following conditions is fulfilled are preferred:

$A_1$ represents a linear alkyl radical comprising from 2 to 12, preferably 2 to 6, in particular 3 carbon atoms, said radical optionally comprising one or more unsaturations;

$A_2$ represents a linear or branched alkyl radical, comprising from 2 to 20 carbon atoms, in particular from 12 to 18 carbon atoms, said radical optionally comprising one or more unsaturations, and even more preferably a group of formula

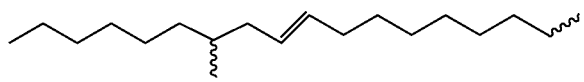

l and m independently represent an integer from 1 to 10, the sum of l+m being, preferably, from 2 to 20;

the sum of l+m has an average value of 5 to 12, in particular 7 or 11, n is an integer from 2 to 8;

D is a linear or branched alkyl radical, comprising from 6 to 14 carbon atoms, said radical optionally comprising one or more unsaturations X is a linear or branched alkyl radical, having or not having unsaturations, comprising from 2 to 10 carbon atoms, in particular 6 carbon atoms.

Y represents an oxygen atom.

Preferred polyurethane compounds of formula (I) are those in which:

$A_1$ represents a linear or branched alkyl radical comprising from 2 to 6, in particular 3, carbon atoms;

$A_2$ represents a linear or branched alkyl radical, comprising from 12 to 18 carbon atoms, said radical optionally comprising one or more unsaturations;

l and m represent, independently of one another, an integer from 1 to 10, the sum of l+m being, preferably, from 5 to 12;

n is an integer from 2 to 8;

D represents a linear or branched alkyl radical, comprising from 6 to 14 carbon atoms, said radical optionally comprising one or more unsaturations;

X is a linear or branched alkyl radical, having or not having unsaturations, comprising from 2 to 10, in particular 6, carbon atoms, and Y represents an oxygen atom.

A preferred polyurethane compound of formula (I) is as defined below:

$A_1 = C_3H_6$, $A_2$ represents a group of formula

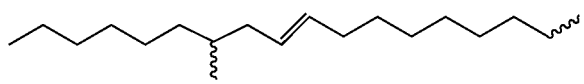

l+m=7 (average value), n is an integer from 2 to 8, $D = C_{10}H_{20}$, $X = C_6H_{12}$, and Y represents an oxygen atom.

The invention also relates to a process for preparing gelling polyurethanes. The preparation of the gelling polyurethane has the aim of synthesizing then chemically modifying an estolide (compounds of the fatty acid polyester type derived from hydroxylated oils, such as castor oil) in order to incorporate urethane groups therein, thus making it possible to provide the gelling properties sought.

According to the invention, said process for preparing gelling polyurethanes comprises the following steps:

1) The functionalization of a di-OH estolide of formula (3) by a diisocyanate derivative of formula (4) in order to obtain a diisocyanate estolide of formula (5)

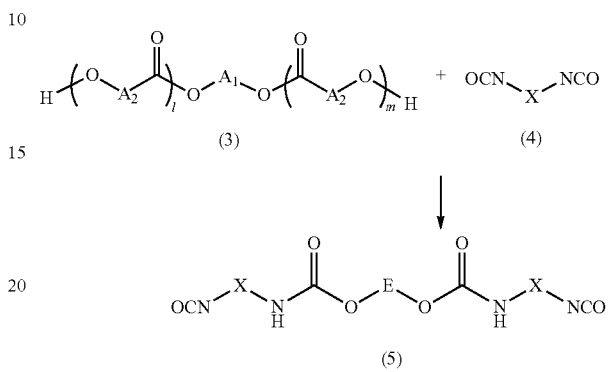

in which:

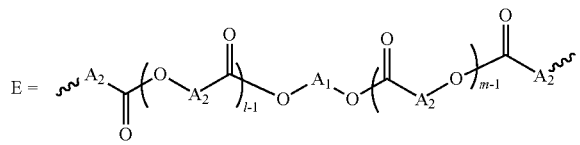

$A_1$ represents a linear or branched alkyl radical, comprising from 2 to 20 carbon atoms, preferably from 2 to 12, and in particular from 2 to 6, said radical optionally comprising one or more unsaturations, optionally being interrupted by at least one heteroatom selected from O, N and S, and being optionally substituted by at least one substituent —OAlk, Alk representing an alkyl group comprising from 1 to 10 carbon atoms;

$A_2$ represents a linear or branched alkyl radical, comprising from 2 to 20 carbon atoms, preferably from 5 to 18, and preferentially from 6 to 17 carbon atoms, said radical optionally comprising one or more unsaturations, and optionally being substituted by at least one substituent —OAlk, Alk representing an alkyl group comprising from 1 to 10 carbon atoms;

l and m represent, independently of one another, an integer from 1 to 20, preferably from 1 to 10, the sum of l+m being, preferably, from 2 to 20;

X is a linear or branched alkyl radical, having or not having unsaturations, comprising from 2 to 20 carbon atoms;

2) The extension of the chain by addition of a difunctional compound (6) capable of reacting with the isocyanates of the compound (5), optionally solubilized in an oil and leading to the polyurethane or similar compound (7) having gelling properties

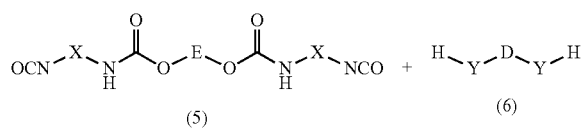

(5)

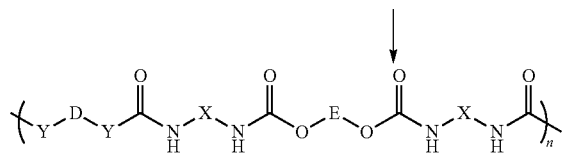

(6)

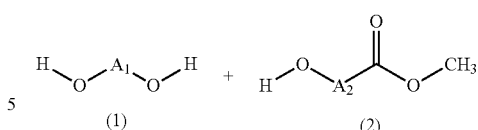

(1)     (2)

↓

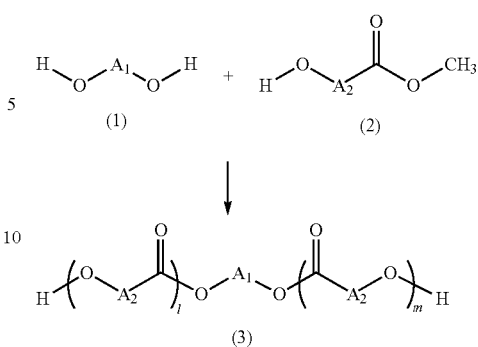

(3)

in which

A$_1$, A$_2$, E, X, l and m are as defined above;

D represents a linear or branched alkyl radical, comprising from 2 to 40 carbon atoms, preferably from 6 to 14 carbon atoms, said radical optionally comprising one or more unsaturations;

n is an integer from 2 to 12, preferably from 2 to 8;

Y represents an atom or a group from: O, NH, S, C(O)O; and 3) optionally, chain termination by addition of a nucleophilic compound capable of reacting with optionally residual isocyanate functions.

Preferably, A$_1$ represents a linear alkyl radical comprising from 2 to 12, preferably 2 to 6, in particular 3 carbon atoms, said radical optionally comprising one or more unsaturations.

Preferably, A$_2$ represents a linear or branched alkyl radical, comprising from 2 to 20 carbon atoms, in particular from 12 to 18 carbon atoms, said radical optionally comprising one or more unsaturations, and even more preferably a group of formula:

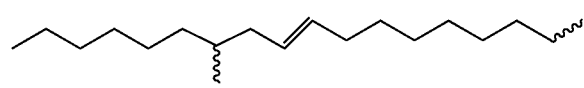

All of the preferred aspects with respect to A$_1$, A$_2$, E, X, l, m, n, D, X and Y mentioned above for the polyurethane compounds of formula (I) also apply to the preparation process according to the invention.

The diisocyanate of formula (4) can be selected, for example, from the non-branched aliphatic diisocyanates comprising 2 to approximately 36 carbon atoms, or from 4 to 30 carbon atoms, such as, for example, hexamethylene diisocyanate (HMDI), 1,10-decane diisocyanate, 1,4-butane diisocyanate (BDI) or 1,12-dodecane diisocyanate.

A diisocyanate preferred for the purposes of the invention is hexamethylene diisocyanate (HMDI).

The diol estolide of formula (3)

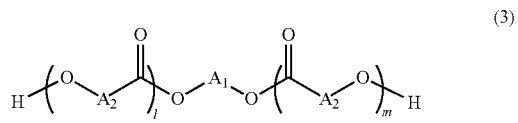

(3)

in which A$_1$, A$_2$, l and m are as defined above, is available commercially, or can by prepared by condensation of a diol (1) with a hydroxylated fatty acid derivative (2):

as is described, for example, in application WO2014/044809.

Reference may be made, for example, more particularly, to the preparation of the compounds of formula (I-2) and (IA-2). The synthesis is described in particular in step 1 of Example 1.

The 1st step, namely the step of functionalization of the di-OH estolide by a diisocyanate derivative has, preferably, a duration comprised between 15 mins and 6 h, preferably between 30 mins and 2 h 30 mins, and is carried out in the presence or in the absence of a solvent of the oil type.

According to the final compound desired, this step of functionalization of the di-OH estolide by a diisocyanate derivative can be carried out, for example, according to 2 alternatives, in the presence or in the absence of a solvent of the oil type, such as for example caprylic/capric triglyceride, namely:

by rapid addition (duration less than approximately 1 min) of the diisocyanate to the diOH estolide (Step 1a), or by slow (duration approximately 15 mins) or rapid (duration less than approximately 1 min) addition of the diOH estolide to the diisocyanate, (1b).

Step 1a promotes the formation of estolide oligomers, while step 1b promotes the functionalization of the chain-ends of the estolides.

Step 1a can be carried out by rapid addition of a quantity of diisocyanate (4) comprised between 1.4 and 2 equivalents in a reactor with mechanical stirring containing 1 equivalent (eq) di-OH estolide (3), calculated according to its OH index.

The reaction is carried out at a temperature comprised between 60° C. and 150° C., preferably between 110° C. and 135° C., in particular between 115° C. and 135° C., in a sealed system dried beforehand and placed under a continuous nitrogen stream. Step 1b can be carried out by addition of 1 equivalent (eq) di-OH estolide (3) within the space of 15 mins over a mixture of oil (for example caprylic/capric triglyceride) and diisocyanate (4) present in a quantity comprised between 1.4 and 2.0 equivalents in a reactor with mechanical stirring. The reaction is carried out at a temperature greater than or equal to 110° C. in a sealed reactor dried beforehand and placed under a continuous nitrogen stream.

The 2nd step of the process according to the invention (synthesis of the polyurethane of diol estolide) can be carried out at a temperature greater than 110° C., in particular greater than 115° C., preferably comprised between 110° C. and 130° C., in particular between 115° C. and 130° C., for a duration comprised between 5 minutes and 2 hours, by addition of one or more nucleophilic difunctional molecules capable of being or not being solubilized in a solvent of the oil type. The nucleophile or nucleophiles is (are) added to the diisocyanate estolide in order to form the gelling agent of the polyurethane type. The ratio between the difunctional nucleophile (6) and the diisocyanate estolide (5) is one of the factors which influences the gelling capacity of the final product. Preferably, a quantity of diol will be used comprised between 0.1 and 2 equivalent(s), and more particularly between 0.4 and 0.8 equivalent (eq) for 1 eq diisocyanate estolide. A preferred diol is 1,10-decanediol. Other cosmetic or non-cosmetic oils having the property of hot solubilization of 1,10-decanediol can be used during this step.

At the end of the 2nd step, the gelling polyurethane is already formed, but can optionally still have residual isocyanate functions. In order to eliminate these unreacted isocyanate functions and to stop the reaction, a nucleophilic molecule of the alcohol, thiol amine or carboxylate type, multifunctional or difunctional, is added in excess to the reaction medium during a 3rd (optional) step at a temperature comprised between 110 and 150° C., in particular between 115° C. and 130° C. This nucleophilic molecule is ideally soluble in the cosmetic oils.

At the end of the 3rd step, the recovery of the gelling polyurethane can be carried out, for example, by causing it to flow it at a temperature greater than 110° C. from the reactor to a suitable recipient.

The process according to the invention has various new features and advantages with respect to those of the prior art. In particular, this process is characterized by short reaction times, as well as by the absence of the formation of by-products that are of low solubility in oils, thus increasing the transparency of the gels once the gelling polyurethane is dissolved in an oil. In addition, it involves mainly compounds of natural origin.

The invention also relates to the use of the gelling polyurethane according to the invention, or obtained according to the process of the invention, as a gelling agent for organic media. In particular, the invention also relates to the use of the gelling polyurethane according to the invention, or obtained according to the process of the invention, as a gelling agent for oils selected, for example, from the organic oils, including vegetable oils, and the mixtures of apolar oils and more-polar oils, such as for example hydrogenated polyisobutene, polyisobutene, etc. (INCI name).

The invention also relates to a process for gelling at least one oil selected, for example, from the organic oils and the mixtures of apolar oils and more-polar oils, in which a gelling polyurethane of formula (I) as described above, according to the invention, or obtained by the process of preparation described above, is added to said oil or oils, or to a composition containing it or them.

The gels comprising the gelling polyurethane according to the invention, or obtained according to the process of the invention, and at least one pharmaceutically or cosmetically acceptable oil are a subject of the invention.

According to a preferred aspect, the gelling polyurethane according to the invention, or obtained according to the process of the invention, makes it possible to form, for example, a strong shear-thinning and thixotropic gel having a content of 5% by weight in caprylic/capric triglyceride. When a constant shear rate of $100\ s^{-1}$ is applied to this gel during 5 minutes, the viscosity reduces from 2.2 to 1.2 Pa.s. This gel then returns to its initial viscosity in 8 hours.

The gelling polyurethanes according to the invention make it possible to form gels in numerous cosmetic oils, such as, for example: C12-C15 alkyl benzoate, dimer dilinoleyl dimer dilinoleate, caprylic/capric triglyceride, isononyl isononanoate, Ricinus communis seed oil, triethylhexanoin, ethylhexyl palmitate, ethylhexyl myristate, dicaprylyl carbonate, isopropyl myristate, isopropyl palmitate, propylene glycol, dicaprylyl carbonate, pentaerythrityl tetraisostearate, ethylhexyl stearate, bis diglyceryl polyacyladipate, Triticum vulgare germ oil, Prunus amygdalus dulcis, Glycine soja oil, Sunflower helianthus oil, Sesamum indicum oil, Butyrospermum Parkii (Shea) Butter, Coco Nucifera (Coconut) Oil, etc. (INCI names). The gelling polyurethanes according to the invention can also gel the apolar oils if they are mixed with more-polar oils, such as, for example, a 50% hydrogenated polyisobutene/50% isopropyle myristate mixture.

The gelling polyurethane according to the invention, or obtained according to the process of the invention, as gelling agent can also be used as a gelling agent for glycols, such as glycerol, propylene glycol or butylene glycol, in particular PEG-40 sorbitan peroleate, PEG-20 glyceryl triisostearate etc.

Also, the gelling polyurethane according to the invention, or obtained according to the process of the invention makes it possible to gel the oils and to stabilize mixtures containing up to 8% waxes with the following waxes: beeswax, C10-18 triglycerides, behenyl alcohol, glyceryl stearate, synthetic wax, pentaerythrityl distearate, copernicia cerifera wax, cetearyl alcohol, cetyl alcohol, ozokerite, rice bran wax, sunflower wax, bis diglyceryl polyacyladipate (INCI names).

The gelling polyurethane also makes it possible to gel oils and stabilize mixtures containing up to 8% by weight of butters with, for example, the following butters: shea butter, argan butter, apricot butter, coconut butter.

The invention also relates to the gels containing or formed from the gelling polyurethane according to the invention, or obtained according to the process of the invention.

The content by weight of gelling polyurethane in said gel can be, for example, comprised between 0.7% and 10%, preferably from 1 to 5%.

A subject of the invention is also compositions comprising gels containing or formed from the gelling polyurethane as described above, in particular pharmaceutical or cosmetic compositions.

Said pharmaceutical or cosmetic compositions can comprise at least one active ingredient and at least one pharmaceutically acceptable or cosmetically acceptable vehicle and/or additives.

The mass content of the gelling polyurethane in a cosmetic composition according to the invention can be, for example, comprised between 0.7% and 10%, preferably from 1 to 5%.

The gelling polyurethanes according to the invention, or obtained according to the process of the invention, can thus be associated in cosmetics with polar, apolar, vegetable oils, glycols, fragrances.

They are, in particular, compatible with organic and mineral sunscreens, pigments and nacres, oily active ingredients currently used in cosmetics, cosmetic butters and waxes or emulsifying agents.

The gelling polyurethanes described above can be incorporated in various anhydrous galenic formulations such as anhydrous gel, sprayable gel, pearlized gel, tinted gel, organic sun gel, inorganic sun gel, fragranced gel, lip balm, gloss, oily make-up removal gel, stick, etc.

They can also be incorporated in formulations of the emulsion type; such as, for example, a gel-cream without emulsifying agent, a water-in-oil emulsion, an oil-in-water emulsion, a mascara, a foundation, a foam, etc.

The invention is illustrated by the following examples.

In the examples, the estolides of propane-1,3-diol (PDO) PRIC212 and PRIC2205H are methyl polyricinoleates marketed by ITERG, (Institut des Corps Gras). HMDI is hexamethylene diisocyanate (Covestro). Labrafac CC (INCI name: Caprylic/Capric Triglyceride) originating from Gattefossé. 1,10-decanediol originates from Beckmann-Kenko GmbH.

The estolide of 1,3-propanediol diOH (3) can also be prepared as described in "Preparation 1" below.

Preparation 1: Synthesis of the Estolide of 1,3-Propanediol diOH (3)

EXAMPLE 1

Preparation of a Polyurethane of Estolide of PDO (PRIC212) and 1,10-Decanediol in which the Steps 1) and 2) are Carried Out at Two Different Temperatures (GSC16179)

The gelling polyurethane was synthesized in three steps by polyaddition of the estolide of PDO diisocyanate with 1,10-decanediol in the presence of a cosmetic oil. It has a content of natural origin of 92.8% according to the standard NF ISO 16128-2.

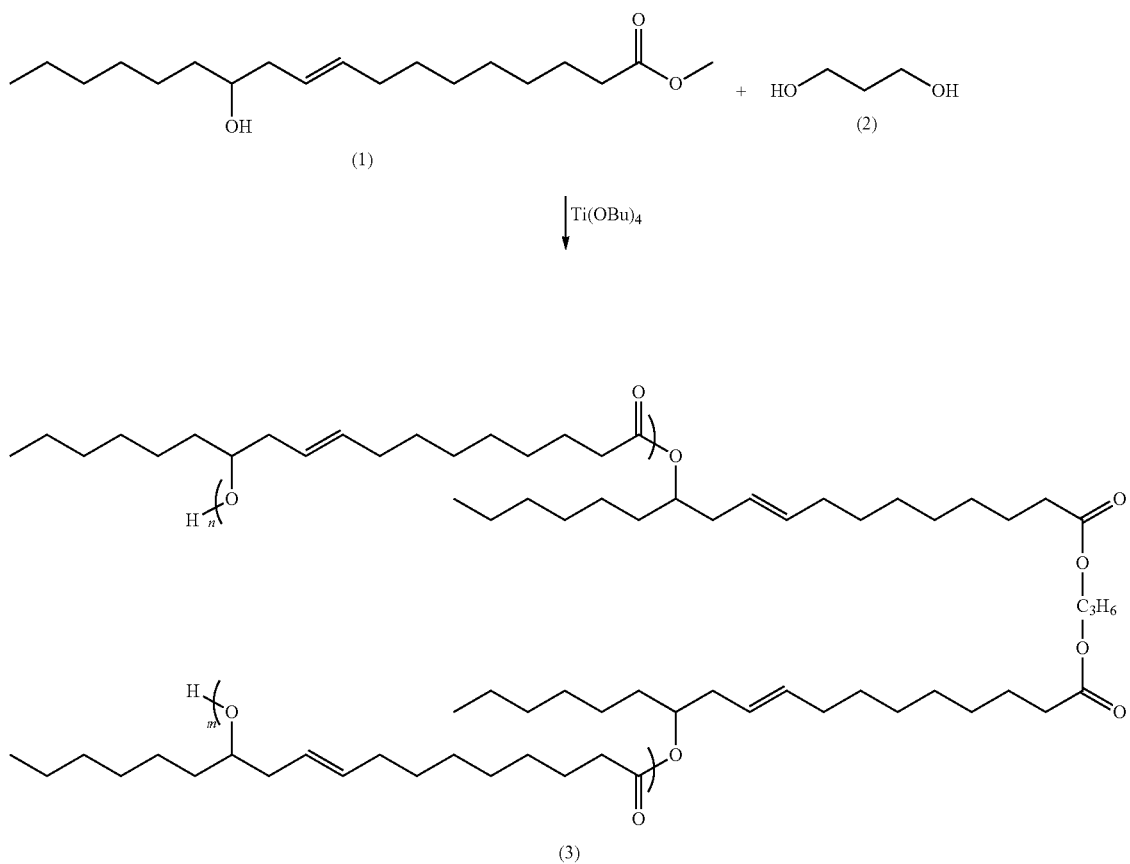

Dihydroxy telechelic poly(methyl ricinoleate) (3) was synthesized by transesterification of the methyl ricinoleate (1) in the presence of 1,3-propanediol as well as Ti(OBu) as described in application WO2014/044809. The methyl ricinoleate (1) utilized was purified beforehand on a chromatography column using a mixture of heptane/acetone (v/v: 98/2) as eluent. The product (1), after purification, has a purity of 99% after analysis by gas phase chromatography.

5 g methyl ricinolate (1), 73 mg 1,3-propanediol (2) as well as 54 mg Ti(OBu) were introduced into a 50 mL flask. The reaction mixture was left under stirring at 140° C. for 2 h under an $N_2$ flow. The temperature was then increased to 180° C. for 1 h then the flask was placed under dynamic vacuum for 21 h at 180° C. At the end of the reaction, the polymer was dissolved in dichloromethane then precipitated from methanol and then dried under reduced pressure until the mass was stabilized.

1) Synthesis of the Estolide of 1,3-Propanediol Diisocyanate (5)

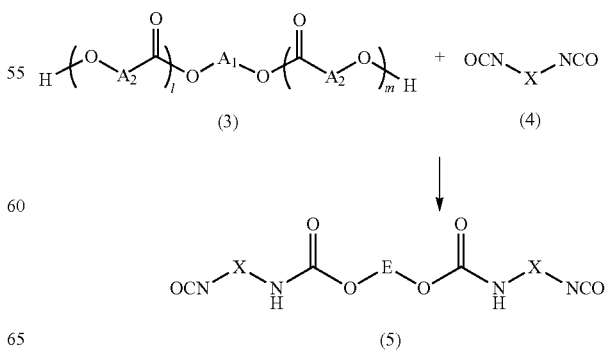

with:

$$E = \phantom{x}^{\sim\sim}A_2 \underset{O}{\overset{O}{\|}}C \left( O - A_2 \underset{O}{\overset{O}{\|}}C \right)_{l-1} O - A_1 - O \left( \underset{O}{\overset{O}{\|}}C - A_2 - O \right)_{m-1} \underset{O}{\overset{O}{\|}}C - A_2 ^{\sim\sim}$$

$X = C_6H_{12}$
$A_1 = C_3H_6$
$A_2$ represents a group of formula

[structure of branched alkenyl chain]

$l+m=7$ (average value)

In a 1 L reactor, 379 g of the estolide of 1,3-propanediol PRIC212 (3) obtained in step 1 dried under vacuum for 2 h 15 at 90° C. and 58 g of HMDI (4) were introduced by rapid addition (<1 min) of (4) over (3). The reaction mixture was left under mechanical stirring at 60° C. for 2.5 h under a nitrogen stream.

2) Synthesis of the Polyurethane of Estolide of 1,3-Propanediol (7)

$$OCN-X-\underset{H}{N}-\underset{O}{\overset{O}{\|}}C-O-E-O-\underset{O}{\overset{O}{\|}}C-\underset{H}{N}-X-NCO \;+\; H-Y-D-Y-H$$

(5)             (6)

↓

$$\left\{ Y-D-Y-\underset{O}{\overset{O}{\|}}C-\underset{H}{N}-X-\underset{H}{N}-\underset{O}{\overset{O}{\|}}C-O-E-O-\underset{O}{\overset{O}{\|}}C-\underset{H}{N}-X-\underset{H}{N}-\underset{O}{\overset{O}{\|}}C \right\}_n$$

With:
$D = C_{10}H_{20}$
$Y = O$ 21.2 g 1,10-decanediol and 162 g Labrafac CC (caprylic/capric triglyceride) are added to the reaction medium, then the temperature is increased to 130° C. The reaction is continued for 30 min after the dissolution of the 1,10-decanediol under nitrogen stream.

3) Synthesis of the Gelling Polyurethane (8)

In order to eliminate the unreacted isocyanate functions and to stop the reaction, 188 g estolide of 1,3-propanediol diOH (3) is added at 130° C. to the 1L reactor of step 3 containing the polyurethane of estolide of 1,3-propanediol (7). The reaction is continued for 1 h until the complete disappearance of the peak associated with NCO in IR (peak at 2250 cm−1).

EXAMPLE 2

Preparation of a Polyurethane of Estolide of PDO (PRIC212) and 1,10-Decanediol in Which the Steps 1) and 2) Are Carried Out at the Same Temperature (GSC17016)

The gelling polyurethane was synthesized in three steps by polyaddition of the estolide of PDO diisocyanate with a chain extender in the presence of a cosmetic oil. It has a content of natural origin of 92.2% according to the standard NF ISO 16128-2.

1) Synthesis of the Estolide of 1,3-Propanediol Diisocyanate (5)

In a 1 L reactor, 103 g Labrafac CC (caprylic/capric triglyceride) is heated to 80° C. under a nitrogen stream and under mechanical stirring (500 rpm). HMDI (40 g) is then added to the mixture and the temperature is increased to 115° C. 20 mins after the addition of the HMDI, propanediol estolide PRIC212 (Mn 2000 g/mol, 238 g) is added over 15 mins by dropping funnel while maintaining the temperature at 115° C. under nitrogen stream. The reaction is continued for 1 h 15.

2) Synthesis of the Polyurethane of Estolide of 1,3-Propanediol (7)

15.5 g 1,10-decanediol is added to the reaction medium at 115° C., and the reaction is continued for 45 mins after the addition.

3) Stopping the Reaction

In order to eliminate the unreacted isocyanate functions and to stop the reaction, 119 g estolide of 1,3-propanediol diOH PRIC212 (Mn 2000 g/mol) is added to the 1 L reactor. The reaction is continued for 1 h until the complete disappearance in IR of the peak associated with the NCO functions.

EXAMPLE 3

Gelling Tests of different oils were carried out with the gelling polyurethanes of examples 1 and 2 (5% by weight).

The results are presented in Table 1 below. The oils are identified by their INCI name.

The gelling agent was dispersed in the oil at 130° C. under stirring.

The strength of the gels was evaluated in the following manner:

The transparency of the gels is evaluated qualitatively, by observation of a pill bottle containing gel. If it is possible to read written characters very clearly through the pill bottle, then the gelling agent is considered as forming transparent gels. The gel is considered to be strong if it does not flow when the pill bottle is tilted.

TABLE 1

| Oils (INCI) | Formation of gels (Example 1) | Formation of gels (Example 2) |
|---|---|---|
| Isopropyl myristate | Strong transparent gel | Strong transparent gel |
| Dicaprylyl carbonate | Strong transparent gel | Strong transparent gel |
| Pentaerythrityl tetraisostearate | Strong transparent gel | Strong transparent gel |
| C12-C15 alkyl benzoate | Strong transparent gel | Strong transparent gel |
| Caprylic/capric triglyceride | Strong transparent gel | Strong transparent gel |
| Ethylhexyl palmitate | Strong transparent gel | Strong transparent gel |
| Isononyl isononanoate | Strong transparent gel | Strong transparent gel |

TABLE 1-continued

| Oils (INCI) | Formation of gels (Example 1) | Formation of gels (Example 2) |
|---|---|---|
| Isopropyl palmitate | Strong transparent gel | Strong transparent gel |
| *Ricinus communis* seed oil | Strong transparent gel | Strong transparent gel |
| Dimer dilinoleyl dimer dilinoleate | Strong transparent gel | Strong transparent gel |

EXAMPLE 4

Measurement of the Viscosity and the Liquefaction Temperature of Gels Produced in Caprylic/Capric Triglyceride with the Polyurethanes of Examples 1 and 2

The viscosity measurements were carried out with a TA Instruments AR1500ex viscosimeter by flow rheology measurement, at shear rates of 100 s$^{-1}$.

The liquefaction temperature was measured under oscillation at 1 Pa and 1 Hz.

The results show a significant viscosity of the gels starting from the presence of 2% gelling agent in the oil, and a liquefaction temperature greater than 50° C., allowing their use in the cosmetics industry.

TABLE 2

| Example | Batch number | Viscosity in Pa · s (shear 100$^{s-1}$ at 20° C., measured at t = 10 s) | | Liquefaction temperature (° C.) (oscillation, 1 Pa, 1 Hz) | |
|---|---|---|---|---|---|
| | | 5% gel in caprylic/capric triglyceride | 2% gel in caprylic/capric triglyceride | 5% gel in caprylic/capric triglyceride | 2% gel in caprylic/capric triglyceride |
| 1 | GSC16179 | 1.33 | 0.38 | Not tested | 68.5 |
| 2 | GSC17016 | 1.01 | 0.26 | 76.3 | 65.1 |

EXAMPLE 5

Synthesis of a Polyurethane of Estolide of 1,3-Propanediol, 1,10-Decanediol and Castor Oil (GSC16162)

The gelling polyurethane was synthesized in three steps by polyaddition of the estolide of 1,3-propanediol diisocyanate with 1,10-decanediol in the presence of two cosmetic oils. It has a content of natural origin of 95.0% according to the standard NF ISO 16128-2.

1) Synthesis of the Estolide of 1,3-Propanediol Diisocyanate (5)

In a 1 L reactor, 194.7 g estolide of 1,3-propanediol (3) and 39.5 g of HMDI (4) were introduced. The reaction mixture was left under mechanical stirring at 60° C. for 2.5 h under a nitrogen stream. Infrared measurements were carried out by monitoring the ratio of —NCO function (peak at 2250 cm−1) with respect to the —CH functions (several bands between 2800 and 3000 cm−1). The reaction is continued until the NCO/CH ratio is constant over at least two measurements separated by 15 mins.

2) Synthesis of the Polyurethane of Estolide of 1,3-Propanediol (7)

14.5 g 1,10-decanediol is solubilized at 130° C. in 86.1 g of Labrafac CC (caprylic/capric triglyceride, Gattefossé). The temperature of the 1 L reactor of step 1 containing the estolide of 1,3-propanediol diisocyanate (5) is increased to 130° C., then the mixture of 1,10-decanediol (6) plus Labrafac CC is added once to the reaction medium. The reaction is continued for 30 mins under nitrogen stream.

3) Synthesis of the Gelling Polyurethane (8)

In order to eliminate the unreacted isocyanate functions and to stop the reaction, 463 g castor oil is added in excess at 130° C. to the 1 L reactor of step 3 containing the polyurethane of estolide of 1,3-propanediol (7). The reaction is continued for 1 h until the complete disappearance of the peak associated with NCO in IR.

EXAMPLE 6

Synthesis of a Polyurethane of Estolide of PDO and Hexanediol (GSC16080)

The gelling polyurethane was synthesized in three steps by polyaddition of the estolide of PDO diisocyanate with 1,6-hexanediol in the presence of a cosmetic oil.

It has a content of natural origin of 92.7% according to the standard NF ISO 16128-2.

1) Synthesis of the Estolide of 1,3-Propanediol Diisocyanate (5)

In a 100 mL flask, 33.2 g estolide of 1,3-propanediol PRIC212 (Mn 2000 g/mol) (3) and 7.2 g of HMDI (4) were introduced. The reaction mixture was left under mechanical stirring at 60° C. for 3.2 h under nitrogen stream.

2) Synthesis of the Polyurethane of Estolide of 1,3-Propanediol (7)

9.72 g estolide of 1,3-propanediol diisocyanate are sampled and placed in a 100 mL flask. 0.48 g 1,6-hexanediol are solubilized at 130° C. in 9.8 g Labrafac CC (caprylic/capric triglyceride, Gattefossé). The temperature of the 100 mL flask containing the estolide of 1,3-propanediol diisocyanate (5) is increased to 130° C., then the mixture of 1,6-hexanediol (6) plus Labrafac CC is added in one go to the reaction medium. The reaction is continued for 2 h 40 under nitrogen stream.

3) Synthesis of the Gelling Polyurethane (8)

In order to eliminate the unreacted isocyanate functions and to stop the reaction, 3.28 g estolide of 1,3-propanediol is added in excess at 130° C. to the 100 L flask of step 2 containing the polyurethane of estolide of 1,3-propanediol (7). The reaction is continued for 2.5 h after the complete disappearance of the peak associated with NCO in IR.

EXAMPLE 7

Synthesis of a Polyurethane of Estolide of PDO and 1,12-Dodecanediol (GSC16071C)

The gelling polyurethane was synthesized in three steps by polyaddition of the estolide of PDO diisocyanate with 1,12-dodecanediol in the presence of cosmetic oil. It has a content of natural origin of 93.4% according to the standard NF ISO 16128-2.

1) Synthesis of the Estolide of 1,3-Propanediol Diisocyanate (5)

In a 250 mL reactor, 35.7 g estolide of 1,3-propanediol PRIC212 (Mn 2000 g/mol) (3) and 8.0 g HMDI (4) were introduced. The reaction mixture was left under mechanical stirring at 60° C. for 1 h under a nitrogen stream, then the mixture is drawn under vacuum for 4 h 30. 43.7 g Labrafac CC (caprylic/capric triglyceride) is added.

2) Synthesis of the Polyurethane of Estolide of 1,3-Propanediol (7)

21.2 g of the previously obtained mixture of estolide of 1,3-propanediol diisocyanate (5) and Labrafac CC are sampled then added to a 250 mL flask at 130° C., then 0.78 g 1,12-dodecanediol is added. The reaction is continued for 1 h under nitrogen stream.

3) Synthesis of the Gelling Polyurethane (8)

In order to eliminate the unreacted isocyanate functions and to stop the reaction, 10 g ethanol is added in excess at 130° C. to the 250 mL flask containing the polyurethane of estolide of 1,3-propanediol (7). The reaction is continued for 1 h until the complete disappearance of the peak associated with NCO in IR. The ethanol is then evaporated in a vacuum for 1 h.

EXAMPLE 8

Gelling tests of oils with the polyurethanes of Examples 5, 6 and 7 (5% by weight gelling polyurethane) are presented in Table 3 below.

TABLE 3

| Oils (INCI) | Example 3 - 4 - 5 |
| --- | --- |
| Isopropyl myristate | Strong transparent gel |
| Caprylic/capric triglyceride | Strong transparent gel |

EXAMPLE 9

Synthesis of a Polyurethane of Estolide (PRIC2205H) and 1,10-Decanediol by Addition of Estolide to the Diisocyanate (LZE17009)

This polyurethane has a content of natural origin of 95.7% according to the standard NF ISO 16128-2.

1) Synthesis of the Estolide PRIC2205H Diisocyanate

In a 250 mL flask, 10 g estolide PRIC2205H (Mn 3000 g/mol) is added dropwise over 15 mins in a mixture containing 0.86 g HMDI and 4 g Labrafac CC (caprylic/capric triglyceride). The reaction mixture was left under magnetic stirring at 115° C. for 1.5 h under a nitrogen stream.

2) Synthesis of the Polyurethane of PRIC2205H and 1,10-Decanediol 0.29 g 1,10-decanediol is added to the reaction medium, maintaining the temperature at 115° C. The reaction is continued for 45 mins.

3) Synthesis of the Gelling Polyurethane

In order to eliminate the unreacted isocyanate functions and to stop the reaction, 5 g estolide PRIC2205H is added in excess to the 250 mL reactor. The reaction is continued for 1 h until the complete disappearance of the peak associated with NCO in IR.

EXAMPLE 10

Synthesis of a Polyurethane of Estolides PRIC2205H and PRIC212, and 1,10-Decanediol by Addition of Estolides to the Diisocyanate (LZE17012)

This polyurethane has a content of natural origin of 94.6% according to the standard NF ISO 16128-2.

1) Synthesis of Estolides PRIC2205H and PRIC212 Diisocyanate

In a 250 mL flask, 1.3 g estolide PRIC212 (Mn 2000 g/mol) then 10 g estolide PRIC2205H (3000 g/mol) is added dropwise in 15 mins to a mixture containing 1.1 g HMDI and 4 g Labrafac CC (caprylic/capric triglyceride). The reaction mixture was left under magnetic stirring at 115° C. for 1.5 h under a nitrogen stream.

2) Synthesis of the polyurethane of PRIC2205H, PRIC212 and 1,10-decanediol 0.42 g 1,10-decanediol is added to the reaction medium, maintaining the temperature at 115° C. The reaction is continued for 45 mins.

3) Synthesis of the Gelling Polyurethane

In order to eliminate the unreacted isocyanate functions and to stop the reaction, 3.25 g estolide PRIC212 is added to the 250 mL reactor. The reaction is continued for 1 h until the complete disappearance of the peak associated with NCO in IR.

The gelling tests of the oils with the polyurethanes of Examples 9 and 10 (5% by weight gelling polyurethane) are presented in Table 4 below.

TABLE 4

| Oils (INCI) | Example 9 | Example 10 |
| --- | --- | --- |
| Caprylic/capric triglyceride | Weak gel | Weak gel |
| PPG 15 Stearyl Ether | Strong gel | Strong gel |
| Dicaprylyl Carbonate | Weak gel | Weak gel |
| Squalane | Weak gel | Strong gel |

EXAMPLE 11

Influence of the Polyurethane Synthesis Conditions on the Viscosity of the Gels Obtained by Dissolution of the Polyurethanes in Caprylic/Capric Triglyceride The flow viscosity measurements at a shear rate of 100 s$^{-1}$ and obtained after 10 s, are recorded in Table 5 below.

TABLE 5

| Table 5Synthesis | GSC16179 (Example 1) | GSC17012 (Example 2) |
|---|---|---|
| Viscosity (Pa·s) - 5% PU | 1.33 | 1.08 |
| T° liq (°C.) - 5% PU | 78.3 | 78.4 |
| Viscosity (Pa·s) - 2% PU | 0.38 | 0.22 |
| T° liq (°C.) - 2% PU | 69 | 67 |
| Viscosity (Pa·s) - 1% PU | 0.10 | Not measured |

It is possible to change the ratio between the PRIC212 (here between Example 1 and Example 2) and the HMDI in order to vary the properties of the gels that will be formed with the gelling agents.

It is also possible to modify the quantities of decanediol during step 2 in order to significantly modify the gelling properties of the polyurethanes, for example by increasing the viscosity of the gels having 5% polyurethane in caprylic/capric triglyceride from 1 to 1.6 Pa.s.

EXAMPLE 12

Incorporating Gelling Polyurethanes in Cosmetic Formulations

Different cosmetic formulas are given below.

For all the cosmetic formulas, the gel was prepared in the following manner: the gelling polyurethane added to the oil is first brought to temperature in a bath, then subjected to vigorous stirring by the Ultra-Turrax® and finally to stirring by a deflocculation blade while maintaining the temperature at 80° C.

The ingredients are named using their INCI name.

1) Fragrance Formula

| INCI | % |
|---|---|
| Caprylic/capric triglyceride | 43.525 |
| PU GSC16179 (Example 1) | 12.50 |
| Fragrance | 43.525 |
| Diethylhexyl syringylidenemalonate (and) caprylic/capric triglyceride | 0.05 |
| Octocrylene | 0.20 |
| Butyl methoxydibenzoylmethane | 0.20 |

The gelling polyurethane is compatible with the fragrances currently used in cosmetics and in the perfume industry.

The gelling polyurethane (for example batch GSC16179 [Example 1]) gels fragrances and forms solid gels with pure fragrance contents comprised between 0.2 and 43.5%. These tests were carried out with 10 different fragrances.

The gelling polyurethane also has a suspensory capacity for holding for example nacres, exfoliating agents, powders of variable density in the medium.

2) Gelled Oil Formula with Nacres in Suspension:

| INCI | % |
|---|---|
| Caprylic/capric triglyceride | 97.8 |
| PU GSC16179 [Example 1] | 1 |
| Synthetic fluorphlogopite (and) iron oxide | 0.1 |
| Fragrance | 0.1 |
| *Caryodendron orinocense* nut oil | 1 |

The gelling polyurethane forms transparent gels making it possible to put elements in suspension starting from 1%. This gel can be formed from numerous gelling polyurethanes according to the invention. This gelled oil is very fluid and vaporizable. The nacres are held in suspension by means of the gelling polyurethane throughout the stability of the product. Nacres having variable granulometries and densities can be used, at concentrations comprised between 0.1 and 1% in the gel.

3) Thick and Vaporizable Pearlized Oil:

| INCI | % |
|---|---|
| Caprylic/capric triglyceride | 92.55 |
| PU GSC16179 [Example 1] | 6.25 |
| Synthetic fluorphlogopite (and) iron oxide | 0.1 |
| Fragrance | 0.1 |
| *Caryodendron orinocense* nut oil | 1 |

In this example of oily jelly, the gel formed remains transparent despite the high content of gelling polyurethane, the nacres are perfectly held in suspension throughout the stability of the product. This gel can be formed from several gelling polyurethanes according to the invention. The gelling polyurethane forms a gel that is transparent, thick, pearlized and sprayable due to the thixotropic rheology of the gel formed.

4) Dry Body Oil

| INCI | % |
|---|---|
| Isononyl isononanoate | 54.5 |
| Isopropyl palmitate | 20 |
| Dicaprylyl carbonate | 20 |
| PU GSC17020 | 5 |
| Tocopheryl acetate | 0.2 |
| Fragrance | 0.3 |

The gelling polyurethane forms a transparent gel in this oil mixture. The gel formed is thick, stable and sprayable. The gelling polyurethane GSC17020 is identical to the batch GSC17016 described in Example 2 but with a quantity of 1,10-decanediol of 0.65 equivalent instead of 0.6 equivalent.

5) Transparent Lip Balm

| INCI | % |
|---|---|
| Isopropyl palmitate | 36.9 |
| Caprylic/capric triglyceride | 30 |
| *Ricinus communis* seed oil | 11.5 |
| Dimer dilinoleyl dimer dilinoleate | 6.4 |
| C10-18 triglycerides | 5.8 |
| PU GSC17020 | 6.4 |
| Bis-diglyceryl polyacyladipate-2 | 3 |

The gelling polyurethane forms a transparent gel in this oil and wax mixture. The gelling polyurethane GSC17020 reduces the crystallization of the waxes and butters which makes it possible to formulate transparent gels for the lips. The gel formed is thick and is easily presented in a jar.

6) Low-Viscosity Lip Gloss

| INCI | % |
| --- | --- |
| Pentaerythrityl tetraisostearate | 30 |
| Dimer dilinoleyl dimer dilinoleate | 20 |
| Ricinus communis seed oil | 46.1 |
| Tocopheryl acetate | 0.2 |
| PU16179 [Example 1] | 2.5 |
| CI 15850, Synthetic Wax | 0.2 |
| Titanium dioxide (and) synthetic fluorphlogopite (and) iron oxide | 1 |
| Fragrance | 0.5 |

The gelling polyurethane forms a transparent gel in this oil mixture. The gelling polyurethane holds the nacres and pigments in suspension. The gel formed is not very thick and is easily presented in a gloss bottle. This gel can be formed with polyurethane GSC16179 [Example 1] or GSC17020. According to the example of gelling polyurethane used, the nacres are not held in suspension.

The gelling polyurethane presents no risk to the labial mucous membranes.

7) Moderate-Viscosity Gloss

| INCI | % |
| --- | --- |
| Pentaerythrityl tetraisostearate | 30 |
| Dimer dilinoleyl dimer dilinoleate | 20 |
| Ricinus communis seed oil | 46.1 |
| Tocopheryl acetate | 0.2 |
| PU GSC16179 [Example 1] | 5 |
| CI 15850, Synthetic Wax | 0.2 |
| Titanium dioxide (and) synthetic fluorphlogopite (and) iron oxide | 1 |
| Fragrance | 0.5 |

The gelling polyurethane forms a transparent gel in this oil mixture. The gelling polyurethane holds the nacres and pigments in suspension. The gel formed is moderately thick and is easily displayed in a gloss bottle. This gel can also be formed with the gelling polyurethanes GSC16100 or GSC17020. The nacres are perfectly held in suspension during the entire length of the stability tests.

The gelling polyurethane presents no risk to the labial mucous membrane.

8) High-Viscosity Gloss That Can Be Presented in a Jar

| INCI | % |
| --- | --- |
| Pentaerythrityl tetraisostearate | 30 |
| Dimer dilinoleyl dimer dilinoleate | 20 |
| Ricinus communis seed oil | 38.6 |
| Tocopheryl acetate | 0.2 |
| PU16179 [Example 1] | 10 |
| CI 15850, synthetic wax | 0.2 |
| Titanium dioxide (and) synthetic fluorphlogopite (and) iron oxide | 1 |
| Fragrance | 0.5 |

The gelling polyurethane forms a transparent gel in this oil mixture. The gelling polyurethane holds the nacres and pigments in suspension. The gel formed is thick and is easily presented in a jar. This gel can also be formed with the gelling polyurethane GSC17020. The nacres are perfectly held in suspension throughout the stability tests (several months).

The gelling polyurethane presents no risk to the labial mucous membrane.

9) Exfoliant for the Body

| INCI | % |
| --- | --- |
| Caprylic/capric triglyceride | 83.40 |
| PU GSC17020 | 6.00 |
| Sucrose | 4.00 |
| Synthetic Wax (and) CI 77891 (and) CI 77510 | 1.00 |
| PEG-20 Glyceryl triisostearate | 5.00 |
| Fragrance | 0.50 |
| Diethylhexyl syringylidenemalonate (and) caprylic/capric triglyceride | 0.10 |
| Hydrogenated palm kernel glycerides and hydrogenated palm glycerides | 5.00 |

The gelling polyurethane makes it possible for example to hold exfoliants of variable density in suspension in an oily gel containing between 5 and 10% gelling polyurethane. The gelling polyurethane holds in suspension, for example, 4% sugar or salt or synthetic wax, or corundum alpha-alumina or pumice stone. The base gel is transparent. The thixotropic aspect of the gel allows fluid spreading, while the product is very thick in a jar.

10) Gelled Sun Oil with Organic Filters

| INCI | % |
| --- | --- |
| Butyl methoxydibenzoylmethane | 3 |
| Octocrylene | 8 |
| Ethylhexyl salicylate | 5 |
| Homosalate | 10 |
| Trimethoxybenzylidene pentanedione | 1 |
| C12-C15 Alkyl benzoate | 67.8 |
| PU GSC16179 [Example 1] | 5 |
| Fragrance | 0.2 |

The gelling polyurethane forms a transparent gel in mixtures containing octocrylene, ethylhexyl salicylate, homosalate, and/or butyl methoxydibenzoylmethane. The gelling polyurethane is compatible and stable with most organic filters. The gel can also be formed with the gelling polyurethane GSC17020.

11) Gelled Sun Oil with Organic and Mineral Filters

| INCI | % |
| --- | --- |
| Butyl methoxydibenzoylmethane | 1.5 |
| Octocrylene | 4 |
| Ethylhexyl salicylate | 2.5 |
| Homosalate | 5 |
| Trimethoxybenzylidene pentanedione | 0.5 |
| Caprylic/capric triglyceride | 50 |
| C12-C15 Alkyl benzoate | 32.4 |
| PU GSC16179 [Example 1] | 2.5 |
| Fragrance | 0.1 |
| Titanium dioxide | 1.5 |

The gelling polyurethane holds inorganic filters in suspension such as for example titanium dioxide in a thick and sprayable gel.

The gel can also be formed with the gelling polyurethane GSC17020.

12) Make-Up Remover Jelly

| INCI | % |
| --- | --- |
| Ethylhexyl cocoate (and) *Cocos nucifera* oil | 20 |
| C12-C15 alkyl benzoate | 20 |
| *Cocos nucifera* oil (and) hydrogenated coconut oil | 3 |
| Caprylic/capric triglyceride | 41.3 |
| PU GSC17020 | 5 |
| PEG-40 Sorbitan peroleate | 10 |
| Tocopheryl acetate | 0.2 |
| Fragrance | 0.5 |

The gelling polyurethane makes it possible to form gels in cleansing oils with a high content of emulsifying agent. The gelling polyurethane is compatible with the oily emulsifying agents.

The gel formed is thick, completely transparent and stable.

13) Water-in-Oil Emulsion

| INCI | % |
| --- | --- |
| Water/aqua | 64.4 |
| Magnesium sulfate | 0.7 |
| Glycerin | 5 |
| Phenoxyethanol (and) ethylhexylglycerin | 0.8 |
| Propanediol | 1 |
| Octyldodecanol (and) octyldecyl xyloside (and) PEG-30 dipolyhydroxystearate | 4 |
| Caprylic/capric triglyceride | 21.6 |
| PU GSC16179 [Example 1] | 2.4 |
| Fragrance | 0.1 |

The gelling polyurethane is easily incorporated in water-in-oil emulsion formulas and increases the viscosity. This emulsion can also be formed with the gelling polyurethane GSC17020.

14) Repairing Night Cream

| INCI | % |
| --- | --- |
| *Butyrospermum parkii* Butter | 5 |
| Polyglyceryl-3 diisostearate | 4 |
| Dicaprylyl carbonate | 15 |
| PU GSC16179 [Example 1] | 5 |
| Water/aqua | 57 |
| Magnesium sulfate | 0.7 |
| Glycerin | 10 |
| 1,2-Hexanediol (and) caprylyl glycol | 0.5 |
| Water (and) alcohol (and) *onopordum acanthium* flower/leaf/stem extract | 2 |
| Perfume | 0.5 |
| Tocopheryl acetate | 0.3 |

This repairing night cream does not show instability when it contains the gelling polyurethane, while the formula that does not contain it is unstable. This emulsion can also be formed with the gelling polyurethane GSC17020.

15) Sun Cream

| INCI | % |
| --- | --- |
| Caprylic/capric triglyceride | 12.85 |
| PU GSC17020 | 5 |
| Octyldodecanol (and) octyldodecyl xyloside (and) PEG-30 dipolyhydroxystearate | 4 |
| C12-C15 alkyl benzoate | 12.85 |
| Sodium chloride | 0.5 |
| Aqua | 44.5 |
| Glycerin | 5 |
| Phenoxyethanol (and) ethylhexylglycerin | 0.5 |
| Zinc oxide (and) caprylic/capric triglyceride (and) polyhydroxystearic acid (and) polyglyceryl-3 polyricinoleate (and) isostearic acid (and) lecithin | 14.3 |
| Fragrance | 0.5 |

The gelling polyurethane makes it possible to increase the viscosity and to stabilize sun emulsions containing mineral filters. This example does not show instability when it contains the gelling polyurethane, while the formula that does not contain it is unstable.

16) Oil-in-Water Formula

| INCI | % |
| --- | --- |
| Aqua Water | 30.9 |
| Glycerin | 30 |
| Ethylhexylglycerin & phenoxyethanol | 1 |
| Cetearyl alcohol | 10 |
| Cetyl alcohol (and) glyceryl stearate (and) PEG-75 stearate (and) ceteth-20 (and) stearath-20 | 2.5 |
| Caprylic/capric triglyceride | 20 |
| Sodium stearoyl glutamate | 0.5 |
| PU GSC17020 | 5 |
| Fragrance | 0.1 |

This formula example shows the gelling polyurethane in a formula having a continuous aqueous phase. The gelling polyurethane is correctly incorporated into the mixture and the formula is stable.

17) Gel-Cream Emulsion

| INCI | % |
| --- | --- |
| Water | 73 |
| Acrylate/C10 C30 alkyl acrylate crosspolymer | 0.6 |
| Tetrasodium EDTA | 0.05 |
| Ethylhexylglycerin & phenoxyethanol | 0.8 |
| Caprylic/capric triglyceride | 20 |
| PU GSC17020 | 5 |
| Triethanolamine | 0.55 |

This formula example shows the gelling polyurethane in a formula having a continuous aqueous phase without emulsifying agent. The gelling polyurethane is correctly incorporated into the mixture and the formula is stable.

18) Waterless Emulsion

| INCI | % |
| --- | --- |
| Propylene glycol | 30.40 |
| Glycerin | 30.00 |
| Sodium polyacrylate | 0.10 |
| Cetearyl alcohol | 2.00 |
| Cetyl alcohol (and) glyceryl stearate (and) PEG-75 stearate (and) ceteth-20 (and) stearath-20 | 2.00 |
| Sodium stearoyl glutamate | 0.50 |
| Caprylic/capric triglyceride | 31.00 |
| PUGSC17020 | 4.00 |

This formula example shows the gelling polyurethane in a formula having a continuous glycol phase. The gelling polyurethane is correctly incorporated into the mixture and the formula is more stable with the gelling polyurethane than without the gelling polyurethane, where it breaks up completely.

19) Oil-in-Water Foam

| INCI | % |
|---|---|
| Caprylic/capric triglycerides | 23 |
| PU GSC16179 (Example 1) | 2 |
| Polyglyceryl-6 distearate (and) jojoba esters (and) polyglyceryl-3 beeswax (and) cetyl alcohol | 3 |
| Hydrogenated palm kernel glycerides and hydrogenated palm glycerides | 2 |
| Water/aqua | 64.15 |
| Phenoxyethanol (and) ethylhexylglycerin | 0.8 |
| Propanediol | 2 |
| Tetrasodium EDTA | 0.05 |
| Poloxamer 407 (and) PPG-12/SMDI copolymer | 3 |

The gelling polyurethane can be incorporated into oil-in-water emulsions of the expanded foam type. The gelling polyurethane is correctly incorporated into the mixture and the formula is stable.

20) Waterproof Mascara Formula

| INCI | % |
|---|---|
| Water/Aqua | 55 |
| Magnesium sulfate | 0.63 |
| Glycerin | 5 |
| Phenoxyethanol (and) ethylhexylglycerin | 0.8 |
| Propanediol | 1 |
| Octyldodecanol (and) octyldecyl xyloside (and) PEG-30 dipolyhydroxystearate | 4 |
| Caprylic/capric triglyceride | 19.57 |
| PU GSC16179 (Example 1) | 2.55 |
| C10-18 triglycerides | 3 |
| Iron oxides, triethoxycaprylylsilane, isononyl isononanoate, ethylene/propylene/styrene copolymer, sorbitan oleate | 6.5 |
| ozokerite | 2 |

The gelling polyurethane makes it possible to formulate highly tinted emulsions such as a mascara. The gelling polyurethane increases the viscosity of the mixture, stabilizes the waxy networks, improves the hold on the brush and application to the lash. The gelling polyurethane is correctly incorporated into the mixture and the formula is stable.

EXAMPLE 13

Measurement of the Viscosity of the Gelling Polyurethane of Example 2 According to the Invention and of the Polyurethane of Example 5 of Application WO2016/090081 in Caprylic/Capric Triglyceride (Comparative Example)

The compound of Example 5 of application WO2016/090081 was prepared as described.

The viscosity measurements were carried out on a 5% by weight gel of each of the polyurethanes under the conditions described in application WO2016/090081 with a TA Instruments AR1500ex viscosimeter by flow rheology measurement, at shear rates of $1\ s^{-1}$ and at 20° C.

The results are presented in Table 6 below.

| Example | Batch number | Viscosity in Pa · s | Appearance |
|---|---|---|---|
| 2 | GSC17016 | 53.6 | transparent |
| 5 application WO2016/090081 (comparative example) | — | 1.7 | translucent |

The results show that the gel containing the polyurethane of Example 2 according to the invention have completely different properties to those of the gel containing the polyurethane of Example 5 of application WO2016/090081, namely a significantly greater viscosity and a transparent appearance.

The invention claimed is:

1. A polyurethane compound suitable for gelling oils, of formula (I)

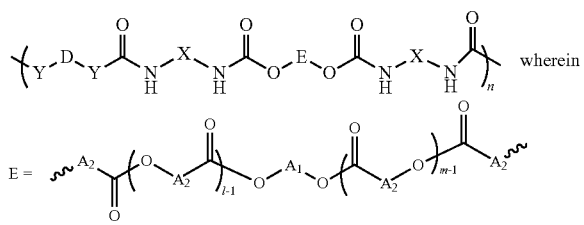

wherein

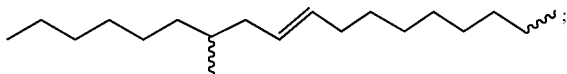

$A_1$ is a linear alkyl radical, comprising 2 to 12 carbon atoms, said radical optionally comprising one or more unsaturations;

$A_2$ is

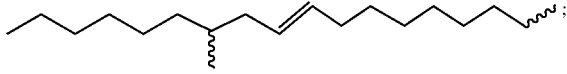

l and m are, independently of one another, an integer from 1 to 10, the sum of l+m being from 2 to 20;

n is an integer from 2 to 12;

D is a linear or branched alkyl radical, comprising 6 to 14 carbon atoms, said radical optionally comprising one or more unsaturations;

X is a linear or branched $C_2$-$C_{10}$ alkyl radical, having or not having unsaturations; and Y is an oxygen atom.

2. The polyurethane compound of formula (I) according to claim 1, wherein $A_1$ represents a linear or branched alkyl radical comprising 2 to 6 carbon atoms;

$A_2$ is l and m represent, independently of one another, an integer from 1 to 10, the sum of l+m being from 5 to 12;

n is an integer from 2 to 8;

D represents a linear or branched alkyl radical, comprising 6 to 14 carbon atoms, said radical optionally comprising one or more unsaturations;

X is a linear or branched alkyl radical, having or not having unsaturations, comprising 2 to 10 carbon atoms; and Y represents an oxygen atom.

3. The polyurethane compound of formula (I) according to claim 1 wherein $A_1$ represents a linear alkyl radical comprising 3 carbon atoms.

4. The polyurethane compound of formula (I) according to claim 1 having a content of natural origin greater than 80% according to standard NF-16128-2.

5. A process for preparing a polyurethane compound of formula (I)

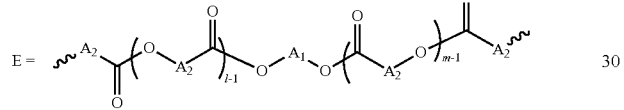
(I)

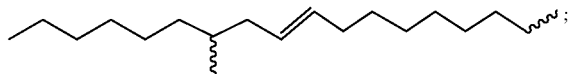

$A_1$ is a linear alkyl radical, comprising 2 to 12 carbon atoms, said radical optionally comprising one or more unsaturations;

$A_2$ is

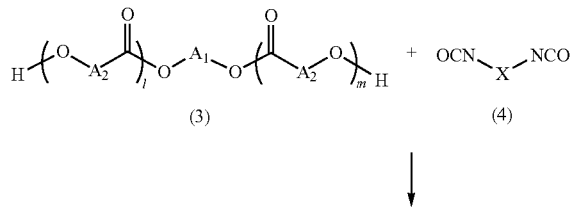

l and m are, independently of one another, an integer from 1 to 20, the sum of l+m being from 2 to 20;

n is an integer from 2 to 8;

D is a linear or branched alkyl radical, comprising from 6 to 14 carbon atoms, said radical optionally comprising one or more unsaturations;

X is a linear or branched $C_2$-$C_{10}$ alkyl radical, having or not having unsaturations;

Y is an oxygen an atom, the process comprising the following steps:

1) functionalizing a di-OH estolide of formula (3) by a diisocyanate derivative of formula (4) in order to obtain a diisocyanate estolide of formula (5)

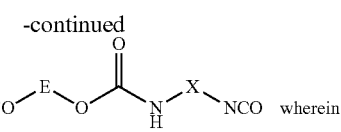
(5)

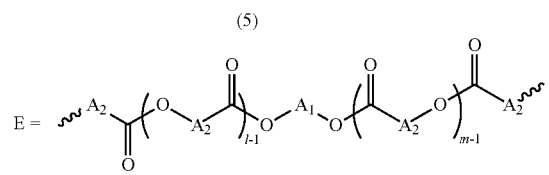

$A_1$, $A_2$, l and m are as defined above;

X is a linear or branched $C_2$-$C_{10}$ alkyl radical, having or not having unsaturations;

2) performing a chain extension in order to obtain a polyurethane of estolide of formula (7) by adding a diol of formula (6), optionally solubilized in an oil

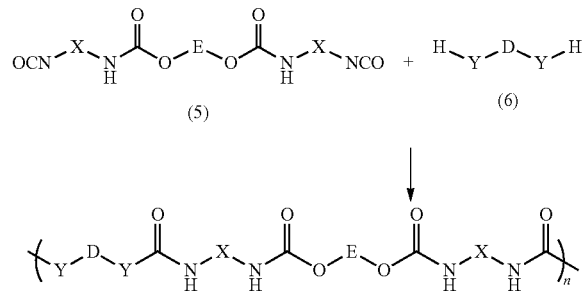

wherein $A_1$, $A_2$, E, X, Y, l and m are as defined above;

D is a linear or branched alkyl radical, comprising 6 to 14 carbon atoms, said radical optionally comprising one or more unsaturations;

n is an integer from 2 to 12;

and 3) optionally, performing chain termination by adding a nucleophilic molecule in excess capable of reacting with the residual isocyanate functions in order to give the gelling polyurethane of formula (I).

6. The process according to claim 5, wherein at least one of the following conditions is fulfilled:

the sum of l+m has an average value of 5 to 12;

n is an integer from 2 to 8.

7. The process of claim 5 wherein $A_1$ represents a linear alkyl radical comprising 3 carbon atoms.

8. The process according to claim 5 wherein the step of functionalization of the di-OH estolide by a diisocyanate derivative is carried out by rapid addition of a quantity of diisocyanate (4) comprised between 1.4 and 2.0 equivalents with respect to 1 equivalent (eq) of di-OH estolide (3), calculated according to its OH index, at a temperature comprised between 60° C. and 150° C.

9. The process according to claim 5 wherein the step of functionalization of the di-OH estolide by a diisocyanate derivative is carried out by adding 1 equivalent (eq) of di-OH estolide (3) over a mixture of oil and diisocyanate (4) present in a quantity comprised between 1.4 and 2.0 equivalents, at a temperature greater than or equal to 110° C.

10. The process according to claim 5 wherein chain termination is carried out by the addition in excess of a nucleophilic molecule of the alcohol, thiol, amine or carboxylate type, mono- or difunctional, capable of reacting with the residual isocyanate functions in excess in the reaction medium at a temperature comprised between 110 and 150° C.

11. An oil gelling agent obtained according to the process of claim 5.

12. A process for gelling at least one oil selected from organic oils, the vegetable oils, and mixtures of apolar oils and more-polar oils, wherein the gelling polyurethane of formula (I) according to claim 1 is added to said at least one oil or oils, or to a composition containing the oils.

13. A gel containing or formed from the gelling polyurethane of formula (I) according to claim 1.

14. The gel according to claim 13, comprising at least one pharmaceutically or cosmetically acceptable oil.

15. The gel according to claim 13, wherein the content by weight of gelling polyurethane of formula (I) is comprised between 0.7% and 10.

16. A pharmaceutical composition comprising the gel according to claim 13.

17. A cosmetic composition comprising the gel according to claim 13.

\* \* \* \* \*